US 8,202,243 B2

(12) United States Patent
Morgan

(10) Patent No.: US 8,202,243 B2
(45) Date of Patent: Jun. 19, 2012

(54) FLUID PRESSURE SENSING CHAMBER

(75) Inventor: Michael D. Morgan, Costa Mesa, CA (US)

(73) Assignee: Novartis AG, Basel (CH)

( * ) Notice: Subject to any disclaimer, the term of this patent is extended or adjusted under 35 U.S.C. 154(b) by 1418 days.

(21) Appl. No.: 11/260,595

(22) Filed: Oct. 27, 2005

(65) Prior Publication Data

US 2007/0098578 A1   May 3, 2007

(51) Int. Cl.
*A61M 31/00* (2006.01)
*F04B 43/12* (2006.01)
(52) U.S. Cl. .......... 604/67; 604/35; 604/131; 417/477.2
(58) Field of Classification Search .................... 604/19, 604/27, 35, 43, 65, 67, 131, 141, 153; 417/477.2, 417/63, 476, 477.5, 477.8
See application file for complete search history.

(56) References Cited

U.S. PATENT DOCUMENTS

| | | |
|---|---|---|
| 4,140,118 A | 2/1979 | Jassawalla |
| 4,187,057 A | 2/1980 | Xanthopoulos |
| 4,479,761 A | 10/1984 | Bilstad et al. |
| 4,493,706 A | 1/1985 | Borsanyi et al. |
| 4,530,647 A | 7/1985 | Uno |
| 4,537,561 A | 8/1985 | Xanthopoulos |
| 4,680,445 A | 7/1987 | Ogawa |
| 4,713,051 A | 12/1987 | Steppe et al. |
| 4,758,238 A | 7/1988 | Sundblom et al. |
| 4,768,547 A | 9/1988 | Danby et al. |
| 4,795,440 A | 1/1989 | Young et al. |
| 4,798,090 A | 1/1989 | Heath et al. |
| 4,798,580 A | 1/1989 | DeMeo et al. |
| 4,838,865 A | 6/1989 | Flank et al. |
| 4,861,242 A | 8/1989 | Finsterwald |
| 4,921,477 A | 5/1990 | Davis |
| 4,923,375 A | 5/1990 | Ejlersen |
| 4,927,411 A | 5/1990 | Pastrone et al. |
| 4,935,005 A | 6/1990 | Haines |
| 4,963,131 A | 10/1990 | Wortrich |
| 5,041,096 A | 8/1991 | Beuchat et al. |
| 5,056,992 A | 10/1991 | Simons et al. |
| 5,106,366 A | 4/1992 | Steppe |
| 5,195,960 A | 3/1993 | Hossain et al. |
| 5,207,647 A | 5/1993 | Phelps |
| 5,267,956 A | 12/1993 | Beuchat |
| 5,302,093 A | 4/1994 | Owens et al. |
| 5,364,342 A | 11/1994 | Beuchat et al. |
| 5,392,653 A | 2/1995 | Zanger et al. |
| 5,403,277 A | 4/1995 | Dodge et al. |
| 5,429,485 A | 7/1995 | Dodge |

(Continued)

FOREIGN PATENT DOCUMENTS

EP   0208955   1/1987

(Continued)

OTHER PUBLICATIONS

European Search Report for EP 06122959.7, Publication No. EP1779878, 2 pages, Dec. 19, 2006.

(Continued)

*Primary Examiner* — Quynh-Nhu H Vu

(57) ABSTRACT

A pressure sensing chamber having a tubing extension extending through the chamber. The tubing contains a plurality of ports so as to allow the purging of air from the chamber, but the ports are sized so that bubbles entering the tubing cannot easily flow into the chamber.

13 Claims, 2 Drawing Sheets

U.S. PATENT DOCUMENTS

| | | | |
|---|---|---|---|
| 5,429,602 A | 7/1995 | Hauser | |
| 5,460,490 A | 10/1995 | Carr et al. | |
| 5,470,312 A | 11/1995 | Zanger et al. | |
| 5,499,969 A * | 3/1996 | Beuchat et al. | 604/30 |
| 5,518,378 A | 5/1996 | Neftel et al. | |
| 5,586,438 A * | 12/1996 | Fahy | 62/78 |
| 5,588,815 A | 12/1996 | Zaleski, II | |
| 5,634,907 A | 6/1997 | Rani et al. | |
| 5,709,539 A | 1/1998 | Hammer et al. | |
| 5,746,708 A | 5/1998 | Giesler et al. | |
| 5,746,719 A | 5/1998 | Farra et al. | |
| 5,759,017 A | 6/1998 | Patton et al. | |
| 5,810,204 A | 9/1998 | Devlin et al. | |
| 5,897,524 A | 4/1999 | Wortrich et al. | |
| 5,906,598 A | 5/1999 | Giesler et al. | |
| 5,910,110 A | 6/1999 | Bastable | |
| 5,927,956 A | 7/1999 | Lim et al. | |
| 5,996,634 A | 12/1999 | Dennehey et al. | |
| 6,012,999 A | 1/2000 | Patterson | |
| 6,059,544 A | 5/2000 | Jung et al. | |
| 6,059,765 A | 5/2000 | Cole et al. | |
| 6,129,699 A | 10/2000 | Haight et al. | |
| 6,235,009 B1 * | 5/2001 | Skow | 604/317 |
| 6,261,283 B1 | 7/2001 | Morgan et al. | |
| 6,272,930 B1 | 8/2001 | Crozafon et al. | |
| 6,293,926 B1 | 9/2001 | Sorensen et al. | |
| 6,364,857 B1 | 4/2002 | Gray et al. | |
| 6,494,694 B2 | 12/2002 | Lawless et al. | |
| 6,572,349 B2 | 6/2003 | Sorensen et al. | |
| 6,592,737 B1 | 7/2003 | Robertson | |
| 6,811,386 B2 | 11/2004 | Hedington et al. | |
| 6,827,709 B2 | 12/2004 | Fujii | |
| 6,955,073 B2 | 10/2005 | Morgan et al. | |
| 6,962,488 B2 * | 11/2005 | Davis et al. | 417/477.2 |
| 7,393,189 B2 | 7/2008 | Davis et al. | |
| 2003/0190244 A1 * | 10/2003 | Davis et al. | 417/477.2 |
| 2005/0186098 A1 | 8/2005 | Davis et al. | |
| 2007/0095143 A1 * | 5/2007 | Gordon et al. | 73/700 |
| 2008/0200878 A1 | 8/2008 | Davis et al. | |
| 2008/0271741 A1 * | 11/2008 | Graham et al. | 128/207.14 |

FOREIGN PATENT DOCUMENTS

| | | |
|---|---|---|
| EP | 1213033 | 6/2002 |
| FR | 2 466 641 A | 4/1981 |
| JP | 07-505542 | 1/1993 |
| JP | 09-178535 | 10/1996 |
| JP | 2000-510239 | 8/2000 |
| JP | 2005-165054 | 6/2001 |
| WO | WO 93/15777 A2 | 8/1993 |
| WO | WO 93/24082 | 12/1993 |
| WO | WO 93/24817 | 12/1993 |
| WO | WO 99/23463 A1 | 5/1999 |

OTHER PUBLICATIONS

European Search Report for EP 06122960.5, Publication No. EP1779879, 2 pages, Dec. 19, 2006.

* cited by examiner

FLUID PRESSURE SENSING CHAMBER

BACKGROUND OF THE INVENTION

The present invention relates generally to fluid pressure sensing chambers and more specifically to fluid pressure sensing chambers used in ophthalmic surgical equipment.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

A typical ultrasonic surgical device suitable for ophthalmic procedures consists of an ultrasonically driven handpiece, an attached cutting tip, and irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draws aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source, usually a peristaltic pump, in the console draws or aspirates the emulsified tissue from the eye through the open end of the cutting tip, the cutting tip and horn bores and the aspiration line and into a collection device. The aspiration of emulsified tissue is aided by a saline flushing solution or irrigant that is injected into the surgical site through the small annular gap between the inside surface of the irrigating sleeve and the cutting tip.

Prior art devices have used sensors that detect irrigation pressure or aspiration vacuum. Based on the information from these sensors, the surgical console can be programmed to respond in order to make the surgical procedure more efficient and safer. In order to reduce the risk of contamination by the aspirated fluid, recent surgical systems use closed pressure sensors, in which the fluid does not come into contact with the load cell or other device used to sense the fluid pressure. One such pressure sensor is illustrated in U.S. Pat. No. 5,392,653 (Zanger, et al.). Overall performance of such closed pressure sensors, however; depend in large part on purging all of the air from the system. Air is much more compressible than the irrigating solution used in surgery, and air pockets or bubbles add compliance to the system. Compliance results in undesirable pressure variations and fluctuations. Common methods of purging air from sealed liquid systems (or "priming" the system) include avoiding sharp edges and abrupt shape changes within the system as well as filling the system with liquid from the bottom or low point of the system. This allows the air to escape out of the top of the system as the systems fills with liquid from below. The inventors of the present invention have discovered that the initial priming of a pressure sensor chambers found within closed surgical fluidic systems is relatively easy, but if bubbles of air are allowed to enter the chamber (for example, if the surgical handpiece is changed mid-procedure), these air bubbles are extremely difficult to purge from the system. This difficulty is the result of the surface tension of the air bubble (as opposed to the unencapsulated air generally involved in the initial priming of the system) causing the bubble to be relatively robust and not easily broken and drawn out of the pressure sensing chamber once introduced. In addition, the liquid "film" surrounding the air bubble is tacky, causing the bubble to stick or adhere to surfaces within the system and resist further movement, even with very high flow rates. One reference, U.S. Pat. No. 6,059,765 (Cole, et al.) has suggested that certain chamber shapes and outlet locations may assist in the removal of air from surgical systems. The inventors have found that the chamber shapes and designs discussed in this reference are insufficient to assure that air bubbles can be purged from the system.

Accordingly, a need continues to exist for a pressure sensing chamber that prevents air from entering the chamber and being trapped within the chamber.

BRIEF SUMMARY OF THE INVENTION

The present invention improves upon prior art peristaltic pumps by providing a pressure sensing chamber having a tubing extension extending through the chamber. The tubing contains a plurality of ports so as to allow the purging of air from the chamber, but the ports are sized so that bubbles entering the tubing cannot easily flow into the chamber.

One objective of the present invention is to provide a cassette a pressure sensing chamber that is easy to prime.

Another objective of the present invention is to provide a pressure sensing chamber that does not permit air bubbles from becoming trapped in the chamber.

Yet another objective of the present invention is to provide a pressure sensing chamber having a tubing extending through the chamber.

These and other advantages and objectives of the present invention will become apparent from the detailed description, drawings and claims that follow.

DETAILED DESCRIPTION OF THE INVENTION

Figure 1:
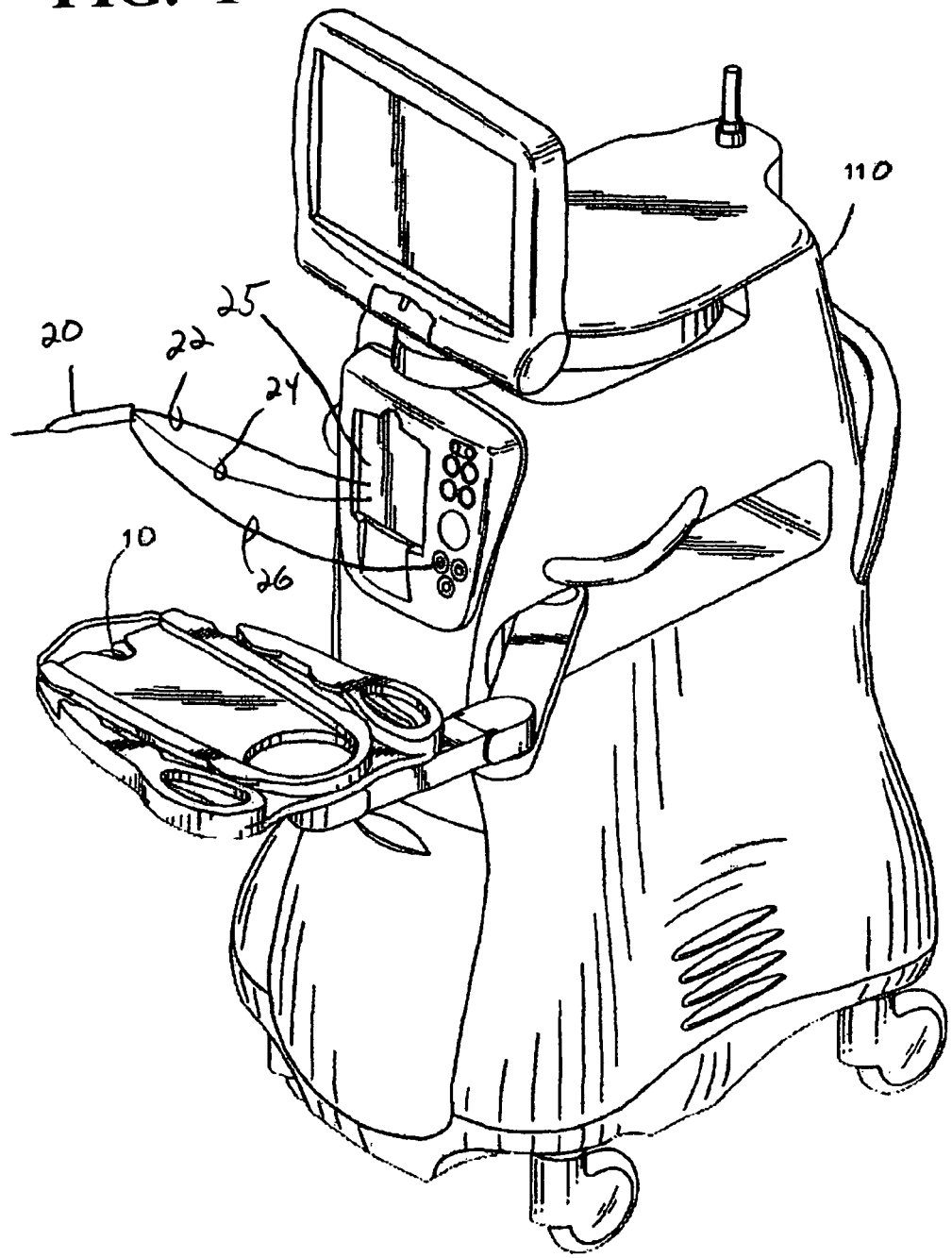
FIG. 1 is a perspective view of a surgical system that may be used with the present invention.
Figures 2, 3:
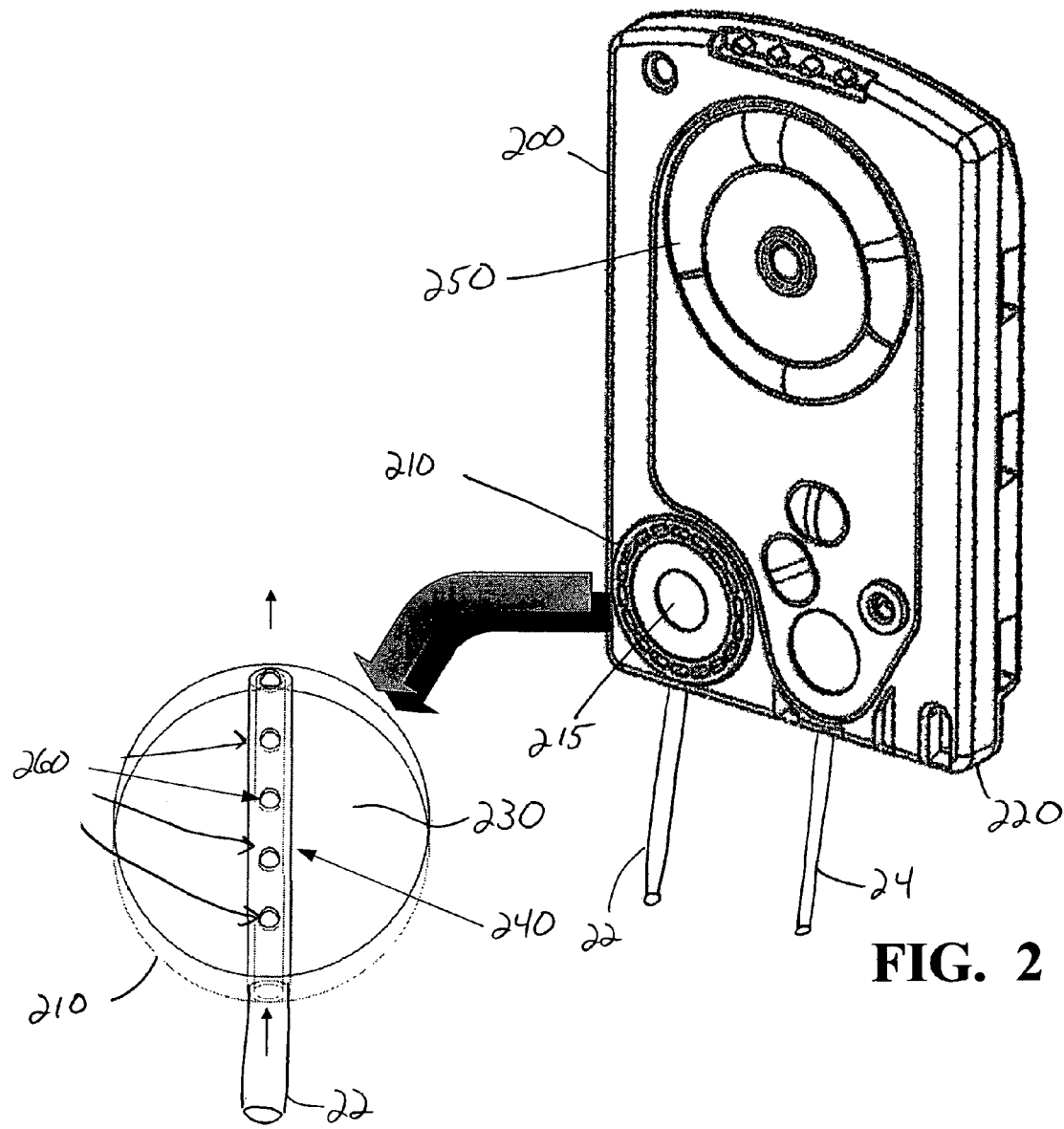
FIG. 2 is a perspective few of a surgical cassette that may be used with the present invention.
FIG. 3 is an enlarged perspective view of a first embodiment of the pressure sensing chamber of the present invention.

As best seen in FIG. 1, commercially available surgical systems generally include surgical console 110 having attached, adjustable mayo tray 10 and handpiece 20 attached to console 110 by aspiration tubing 22, irrigation tubing 24 and power cable 26. Power to handpiece 20 as well as the flows of irrigation and aspiration fluid is controlled by console 110, which contains appropriate hardware and software, such as power supplies, pumps, pressure sensors, valves, all of which are well-known in the art. As best seen in FIG. 2, cassette 200 that may be used with the present invention receives aspiration tubing 22 and irrigation tubing 24 and is installed within cassette receiving portion 25 of console 110. Cassette 200 contains a pressure sensing chamber 210 which may consist of hollow void 230 formed within body 220 of cassette 200 and enclosed by pressure sensing diaphragm 215. Cassette 200 may be any of a variety of commercially available surgical cassettes such as the INFINITI® Fluid Management System available from Alcon Laboratories, Inc., Fort Worth, Tex. Body 220 is generally molded from a suitable thermoplastic.

As best seen in FIG. 3, chamber 210 contains tubing extension 240 that extends through void 230, essentially bisecting void 230 into two identical hemispheres, although other shapes from chamber 210 and void 230 may also be used. Tubing extension may be integrally molded into body 220, or may be integrally formed with aspiration tubing 22. In either case, tubing extension 240 fluidly communicates with aspiration tubing 22 so as to draw fluid through aspiration tubing 22 and into peristaltic pump 250, as indicated by the flow arrows in FIG. 3. Penetrating through tubing extension 240 is one or more holes 260 that allow fluid communication between aspiration tubing 22, void 230 and diaphragm 215. Such fluid communication allows for changes in pressure within aspiration tubing 22 to be communicated to void 230, causing deflection in diaphragm 215 which may be sensed by a load cell (not shown) mounted within cassette receiving portion 25 of console 110. Holes 260 also allow void 230 to be purged of air during initial priming of cassette 200. More importantly, holes 260 are sized and shaped so that any air bubbles entering aspiration line 22 cannot easily flow through holes 260 and enter void 230. The hole(s) 260 locations and size promote good bubble retention within the tubing extension 240 and yet allow fluid flow through the lower hole(s) 260 during initial liquid filling of void 230.

This description is given for purposes of illustration and explanation. It will be apparent to those skilled in the relevant art that modifications may be made to the invention as herein described without departing from its scope or spirit.

I claim:

1. A cassette, comprising:
a) a body;
b) a pressure sensing chamber formed in the body; and
c) a tubing extension extending through the pressure sensing chamber and having an inner diameter, the tubing extension having at least one hole within the pressure sensing chamber that fluidly communicates with the pressure sensing chamber, the at least one hole being sized and shaped smaller than the inner diameter of the tubing extension so that any air bubbles entering the tubing extension are inhibited from entering the pressure sensing chamber;
wherein the tubing extension extends completely through the pressure sensing chamber.

2. The cassette of claim 1 wherein the pressure sensing chamber comprises a hollow void formed in the body enclosed by a pressure sensing diaphragm.

3. The cassette of claim 1 wherein the at least one hole is between approximately 0.0002 square inches to 0.02 square inches in area.

4. The cassette of claim 1 wherein the tubing extension is integrally formed in the body.

5. The cassette of claim 1 further comprising an aspiration tubing connected to the cassette and the tubing extension is formed as a part of the aspiration tubing.

6. A cassette, comprising:
a) a body;
b) a pressure sensing chamber formed in the body, the pressure sensing chamber being formed as a hollow void in the body enclosed by a pressure sensing diaphragm; and
c) a tubing extension integrally formed in the body having an inner diameter and extending through the pressure sensing chamber, the tubing extension having a plurality of holes within the pressure sensing chamber that fluidly communicate with the pressure sensing chamber, the holes being sized and shaped smaller than the inner diameter of the tubing extension so that any air bubbles entering the tubing extension are inhibited from entering the pressure sensing chamber;
wherein the tubing extension extends completely through the pressure sensing chamber.

7. The cassette of claim 6 wherein the holes are between approximately 0.0002 square inches to 0.02 square inches in area.

8. The cassette of claim 6 further comprising an aspiration tubing connected to the cassette.

9. A surgical system, comprising:
a) a surgical console having a cassette receiving portion;
b) a surgical cassette received by the console in the cassette receiving portion, the cassette having
i) a body;
ii) a pressure sensing chamber formed in the body; and
iii) a tubing extension extending through the pressure sensing chamber and having an inner diameter, the tubing extension having a plurality of holes within the pressure sensing chamber that fluidly communicate with the pressure sensing chamber, the holes being sized and shaped smaller than the inner diameter of the tubing extension so that any air bubbles entering the tubing extension are inhibited from entering the pressure sensing chamber;
wherein the tubing extension extends completely through the pressure sensing chamber.

10. The surgical system of claim 9 wherein the pressure sensing chamber comprises a hollow void formed in the body enclosed by a pressure sensing diaphragm.

11. The surgical system of claim 9 wherein the holes are between approximately 0.0002 square inches to 0.02 square inches in area.

12. The surgical system of claim 9 wherein the tubing extension is integrally formed in the body.

13. The surgical system of claim 9 further comprising an aspiration tubing connected to the cassette and the tubing extension is formed as a part of the aspiration tubing.

* * * * *